(12) United States Patent
Rabbani et al.

(10) Patent No.: US 12,122,921 B2
(45) Date of Patent: Oct. 22, 2024

(54) FLUORESCENCE QUENCHER POLYMER CONJUGATES AND USES THEREOF

(71) Applicant: Enzo Biochem, Inc., New York, NY (US)

(72) Inventors: Elazar Rabbani, New York, NY (US); Jack Coleman, East Northport, NY (US)

(73) Assignee: ENZO BIOCHEM, INC., Farmingdale, NY (US)

( * ) Notice: Subject to any disclaimer, the term of this patent is extended or adjusted under 35 U.S.C. 154(b) by 596 days.

(21) Appl. No.: 17/363,637

(22) Filed: Jun. 30, 2021

(65) Prior Publication Data

US 2022/0025188 A1    Jan. 27, 2022

Related U.S. Application Data

(60) Provisional application No. 63/055,375, filed on Jul. 23, 2020.

(51) Int. Cl.
*C09K 11/06*    (2006.01)
*C09B 67/00*    (2006.01)

(52) U.S. Cl.
CPC .............. *C09B 68/41* (2013.01); *C09K 11/06* (2013.01)

(58) Field of Classification Search
USPC ....................................................... 528/169
See application file for complete search history.

(56) References Cited

U.S. PATENT DOCUMENTS

| 5,248,770 A | 9/1993 | Jacobson et al. |
|---|---|---|
| 9,957,393 B2 | 5/2018 | Li |
| 2011/0305685 A1 | 12/2011 | Tseng et al. |
| 2014/0114048 A1 | 4/2014 | Benson et al. |
| 2015/0056711 A1 | 2/2015 | Lei et al. |
| 2015/0238638 A1 | 8/2015 | Han et al. |
| 2016/0289779 A1 | 10/2016 | Li et al. |
| 2020/0085742 A1 | 3/2020 | Lin et al. |

FOREIGN PATENT DOCUMENTS

| WO | WO2016/100983 | 6/2016 |
|---|---|---|

OTHER PUBLICATIONS

CN1209146A Machine Translation (Year: 1999).*
International Search Report and Written Opinion of PCT/US2021/039813 (filed on Jun. 30, 2021 by Enzo Biochem, Inc.); Search and Opinion completed on Sep. 16, 2021 and mailed on Oct. 20, 2021; 8 pages.
Jager et al., "Branched and linear poly(ethylene imine)-based conjugates: synthetic modification, characterization, and application," *Chem Soc Rev*, vol. 41, pp. 4755-4767 (2012).
Extended European Search Report for EP 21846981.5, dated Aug. 13, 2024, 6 pages.

* cited by examiner

*Primary Examiner* — Terressa Boykin
(74) *Attorney, Agent, or Firm* — Quarles & Brady LLP

(57) ABSTRACT

The invention provides chemical conjugates comprising a plurality of fluorescence quenching moieties conjugated to polymer and the use of such conjugates to quench the emission of fluorescence from emitters including macromolecular fluorescent emitters such as phycoerythrin.

15 Claims, 3 Drawing Sheets

FLUORESCENCE QUENCHER POLYMER CONJUGATES AND USES THEREOF

CROSS-REFERENCE TO RELATED APPLICATIONS

This application claims the benefit of U.S. provisional application Ser. No. 63/055,375 filed Jul. 23, 2020 which is hereby incorporated by reference in its entirety.

FIELD OF THE INVENTION

The present invention relates to the field of fluorescence quenching compounds.

BACKGROUND OF THE INVENTION

Phycoerythrin is a red protein-pigment complex from the light-harvesting phycobiliprotein family that is naturally present in red algae and cryophytes as an accessory to the main chlorophyll pigments responsible for photosynthesis. Like all phycobiliproteins, phycoerythrins are composed of protein subunits covalently bound to chromophores called phycobilins. In the phycoerythrin family, two phycobilins are phycoerythrobilin, the typical phycoerythrin acceptor chromophore, and phycourobilin. Typically, phycoerythrins are composed of ($\alpha\beta$) protein subunits, usually organized in a disk-shaped trimer ($\alpha\beta$)3 or hexamer ($\alpha\beta$)6, and a third type of protein subunit, the y chain.

What is needed and provided by the present invention are new and improved fluorescence quenching compounds capable of interacting with and quenching fluorescent emissions from strong macromolecular emitters of fluorescence such as phycoerythrin.

SUMMARY OF THE INVENTION

One embodiment of the invention provides a fluorescence quenching compound that includes:
- a plurality of discrete fluorescence quenching moieties such as EQ0, EQ1 and/or EQ2; and
- a polymer, such as a non-protein, non-nucleic acid polymer such as branched polyethylenimine, wherein each of the plurality of discrete fluorescence quenching moieties is chemically conjugated to a discrete site of the polymer.

A related embodiment of the invention provides a composition that includes:
- the aforementioned fluorescence quenching compound; and
- a fluorescence emitter whose fluorescent emission is capable of being quenched by the compound.

The fluorescence emitter may, for example, be a macromolecular fluorescence emitter, such as phycoerythrin.

Another embodiment of the invention provides a method for manufacturing a fluorescence quenching compound that includes the steps of:
- providing a fluorescence quenching compound that includes an amine reactive group such as but not limited to an NETS-ester or sulfo-NHS ester;
- providing branched polyethylenimine; and
- reacting the fluorescence quenching compound that includes the amine reactive group with the branched polyethylenimine to form a conjugate of the fluorescence quenching compound and the branched polyethylenimine.

Additional features, advantages, and embodiments of the invention may be set forth or apparent from consideration of the following detailed description, drawings if any, and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

Figure 1:
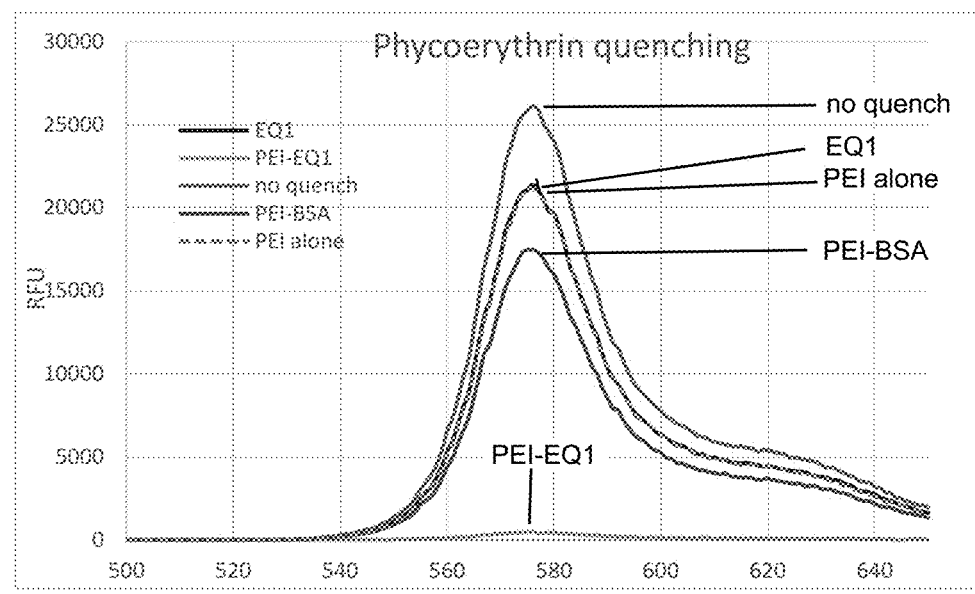
FIG. 1 shows the fluorescence quenching effect on phycoerythrin by a polymeric quencher embodiment of the invention and comparator compounds.

In one aspect, the invention provides fluorescence quenching compounds that are chemical conjugates of multiple fluorescence quenching moieties such as EQ0, EQ1 and/or EQ2 and a polymer, such as a non-protein polymer, such as branched polyethylenimine. The fluorescence quenching moieties conjugated to the polymer may be all the same or may include different fluorescence quenching moieties (different chemical structures).

Polymers containing a multitude of primary amine groups, such as branched polyethylenimine, can be readily conjugated to chemical derivatives of fluorescence quenching compounds that include an amine reactive group such as an N-hydroxysuccinimide ester (NHS ester) or a sulfo-NHS ester as known in the art.

NHS esters are reactive groups formed by carbodiimide-activation of carboxylate molecules. NHS ester-activated crosslinkers and labeling compounds react with primary amines in physiologic to slightly alkaline conditions (pH 7.2 to 9) to yield stable amide bonds. The reaction releases N-hydroxysuccinimide (NHS).

NETS-ester crosslinking reactions are most commonly performed in phosphate, carbonate-bicarbonate, HEPES or borate buffers at pH 7.2 to 8.5 for 0.5 to 4 h at room temperature or 4° C. Primary amine buffers such as Tris (TBS) are not compatible, because they compete for reaction; however, in some procedures, it is useful to add Tris or glycine buffer at the end of a conjugation procedure to quench (stop) the reaction.

Sulfo-NHS esters are similar to NETS esters but contain a sulfonate ($-SO3$) group on the N-hydroxysuccinimide ring. This charged group has no effect on the reaction chemistry, but it does tend to increase the water-solubility of crosslinkers containing them.

Quenchers

Any suitable fluorescence quenching compounds and reactive derivatives thereof, for example, NHS-ester derivatives thereof, for conjugation to a polymer may be used according to the invention, such as but not limited to those disclosed in U.S. Pat. No. 9,957,393 entitled Monoazo Dyes with Cyclic Amine as Fluorescence Quenchers, which is incorporated by reference herein in its entirety.

Without limitation, the following NHS ester derivatives of quenchers may be used according to the invention.

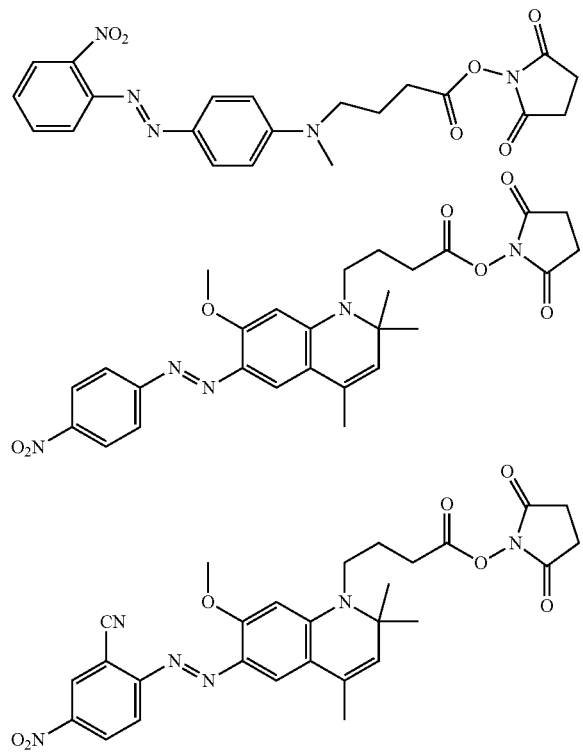

EQ0 NHS ester (Cat. No. ENZ-CHM208-0001; Enzo Life Sciences, Inc., Farmingdale, NY, USA) is an amine-reactive quencher dye. EQ0 has a broad visible absorption with a maximum absorption at 445 nm but no detectable fluorescence emission, making it useful as an acceptor in Förster resonance energy transfer (FRET) applications. It can be used to quench reporter dyes: AMCA, AMCA-X, DEAC, DEAC-X, MCA, MCC, CF™ 350, CF™ 405S, CF™405M, Pacific Blue™, Cascade Blue®, Marina Blue®, Alexa Fluor® 350, Alexa Fluor® 405, DyLight® 350, DyLight® 405, ATTO 390, ATTO 425, ATTO 465, iFluor™ 350, iFLuor™ 405, BD Horizon V450, BUV395, and eFluor®450.

EQ1 NHS ester (Cat. No. ENZ-CHM165-0001; Enzo Life Sciences, Inc., Farmingdale, NY, USA) is an amine-reactive quencher dye. EQ1 has a broad visible absorption with an absorption maximum at 535 nm but no detectable fluorescence emission, making it useful as an acceptor in Förster resonance energy transfer (FRET) applications. It can be used to quench reporter dyes: FAM, Cy2, TET, JOE, VIC, HEX, Cy3, NED, TAMRA, Cy3.5, ROX, Texas Red, Quasar® 570, CAL Fluor® Gold 540, CAL Fluor® Orange 560, CAL Fluor® Red 590, CAL Fluor® Red 610, Alexa Fluor® 430, Alexa Fluor® 488, Alexa Fluor® 532, Alexa Fluor® 546, Alexa Fluor® 555, Alexa Fluor® 568, Alexa Fluor® 594, DyLight® 488, DyLight® 550, DyLight® 594, ATTO 488, ATTO 520, ATTO 532, ATTO Rho6G, ATTO 550, ATTO 565, ATTO Rho11, ATTO 590, and ATTO 594.

EQ2 NHS ester (Cat. No. ENZ-CHM166-0001; Enzo Life Sciences, Inc., Farmingdale, NY, USA) is an amine-reactive quencher dye. EQ2 has a broad visible absorption with an absorption maximum at 583 nm but no detectable fluorescence emission, making it useful as an acceptor in Förster resonance energy transfer (FRET) applications. It can be used to quench reporter dyes: TET, JOE, VIC, HEX, Cy3, NED, TAMRA, Cy3.5, ROX, Texas Red, Cy5, Quasar® 570, Pulsar® 650, CAL Fluor® Gold 540, CAL Fluor® Orange 560, CAL Fluor® Red 590, CAL Fluor® Red 610, CAL Fluor® Red 635, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, DyLight® 550, DyLight® 594, DyLight® 633, DyLight® 650, ATTO 520, ATTO 532, ATTO Rho6G, ATTO 550, ATTO 565, ATTO Rho11, ATTO 590, ATTO 594, ATTO 633, ATTO Rho14, and ATTO 647.

Polymers

Polymers, linear or branched, having multiple discrete sites for conjugation of one or more types of fluorescence quenchers may be used according to the invention. The polymers may, for example, not be proteins or polypeptides. The polymers may, for example, not be polynucleic acid polymers. The polymers may, for example, be synthetic polymers. The polymers may, for example, consist predominantly or only of carbon, nitrogen and hydrogen atoms. The polymer may, for example, be a polyamine.

One polymer that may be used is branched polyethylenimine, a water soluble polyamine with high cationic charge density, which contains primary, secondary, and tertiary amine groups. See, e.g., Jäger M, Schubert S, Ochrimenko S, Fischer D, Schubert US. (2012), Branched and linear poly(ethylene imine)-based conjugates: synthetic modification, characterization, and application, Chem Soc Rev. 41(13):4755-4767. Commercially marketed products are available with a variety of molecular weights and include, for example, branched polyethylenimine, Mw 600 (bPEI 600; Cat. No. 02371-100; Polysciences, Inc., Warrington, PA, USA) and branched polyethylenimine solution Mn~60,000 Mw 750,000 50% w/v in H$_2$0 (Cat. No. P3143 Millipore Sigma, St. Louis, MO, USA).

Embodiments of the present invention may, for example, use branched polyethylenimine having molecular weights of: below Mw 1000; at or above Mw 1000; at or above Mw 5,000; at or above Mw 10,000; at or below Mw 100,000; at or below Mw 1,000,000; and/or in the range of Mw 100 to 1,000,000 or any subrange between whole integer values therein.

EXAMPLE

Production of PEI-EQ1 Conjugate

Branched polyethylenimine solution 50% w/v in H$_2$O ("PEI;" Cat. No. P3143 Millipore Sigma, St. Louis, MO, USA) was diluted in water, specifically 1 µl into 423 µl of water for a final concentration of 1.179 mg/ml PEI or about 27.4 mM of monomer amine.

The control used was bovine serum albumin ("BSA;" Cat. No. AM2618, Thermo Fisher Scientific) with a concentration of 50 mg/ml or about 0.0643 mM of amine (lysines or arginines).

PEI and BSA were buffer exchanged into 100 mM sodium carbonate buffer, pH 9.6 (Cat. No. C33041-50 CAP, Millipore Sigma) using Zeba 7K MWCO columns (Cat. No. 89882, Thermo Fisher Scientific). To do this, the columns were first spun at 1.5k×g for 1 minute to remove the liquid. The column was rehydrated with 300 µl of 100 mM sodium carbonate, pH 9.6 followed by centrifugation at 1.5k×g for 1 minute. The sodium carbonate wash was repeated 3 additional times. The Zeba column was transferred to a fresh tube, and 100 µl of either PEI or BSA was layered on top, followed by centrifugation at 1.5k×g for 1 minute. The flow thru contained either PEI or BSA in sodium carbonate buffer.

1 mg of EQ1-NHS ester (Cat. No. ENZ-CHM165-0001, Enzo Life Sciences, Inc.) was resuspended in 186.7 μl amine-free dimethyl formamide (Cat. No. 43465-AP, Alfa Aesar) to make a 10 mM solution.

For labeling, 100 μl of PEI or BSA was used. For PEI, 68.5 μl of EQ1-NHS ester was added, and for BSA 1 μl of EQ1-NHS ester was added. The reaction was carried out for 3 hours at room temperature (22° C.) for 3 hours on a rotator.

After the reaction, the mixture was purified and buffer exchanged using Zeba columns pre-equilibrated with 50 mM sodium phosphate, pH 8 100 μl at a time. The Zeba columns separate unincorporated EQ1-NHS ester from the larger molecular weight PEI or BSA.

The concentration of EQ1 conjugated to PEI, to BSA or alone was determined by absorbance. EQ1 absorbs at about 535 nm, and has an extinction coefficient of 35.2 mM$^{-1}$ cm$^{-1}$. In this case, the EQ1 concentration alone was 94.5 μM, the concentration of EQ1 conjugated to PEI was 983 μM, and the concentration of EQ1 conjugated to BSA was 36 μM.

EXAMPLE

Quenching with PEI-EQ1 Conjugate

To test if PEI-EQ1 enhances quenching of phycoerythrin compared to EQ1 alone, the quenchers were mixed with 200 ng of a phycoerythrin labeled anti HPV16-E7 antibody, "HPV16 E7 Antibody (ED17) PE" (Cat. No. sc-6981 PE, Santa Cruz Biotechnology, Inc., Dallas, TX, USA). The amount of EQ1 was 394 pmoles in a volume of 110 μl in PBS. As a control, PEI alone at the same concentration was added. Fluorescence was measured on a Biotek SynergyMx plate reader, reading from the top, with excitation at 480 nm, and emission capture from 500 to 650 nm.

The results of this experiment are shown in FIG. 1. As shown, PEI alone has a very minor effect on the fluorescence of phycoerythrin, as does EQ1 alone or EQ1-BSA conjugate. However, when EQ1 conjugated to PEI (EQ1-PEI) is used, the fluorescence of phycoerythrin is reduced to less than 2% of the fluorescence that occurs without any quencher present.

Figure 2:
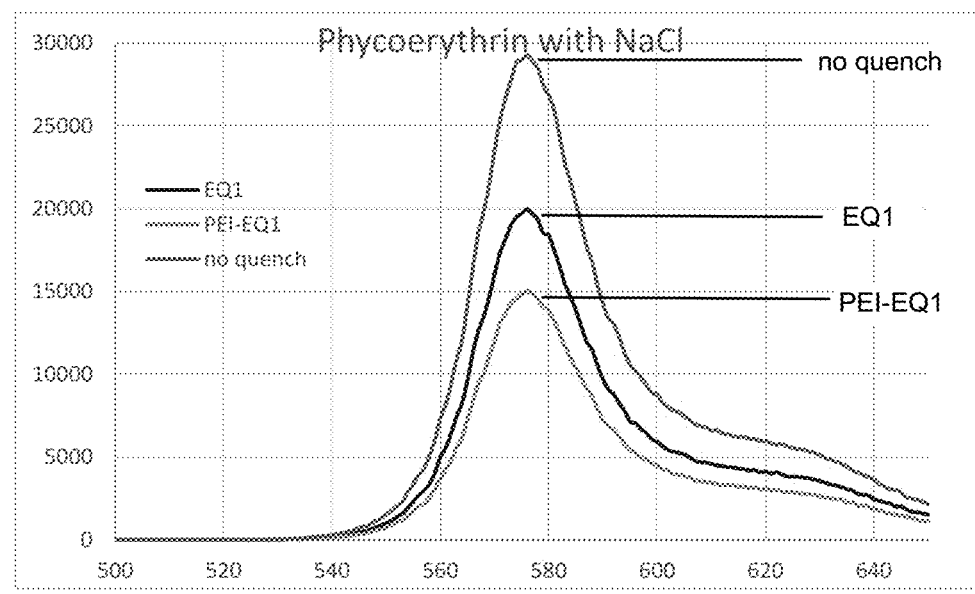
FIG. 2 shows the effect of sodium chloride on fluorescence quenching of phycoerythrin by a polymeric quencher embodiment of the invention.

As shown in FIG. 2, if sodium chloride is added to a concentration of 833 mM, quenching with EQ-PEI is only 50% of the phycoerythrin alone fluorescence. This result suggests that the enhancement of quenching by EQ1-PEI vs. EQ1 alone is related to salt bridge formation between the PEI component of the conjugate and the phycoerythrin.

Figure 3:
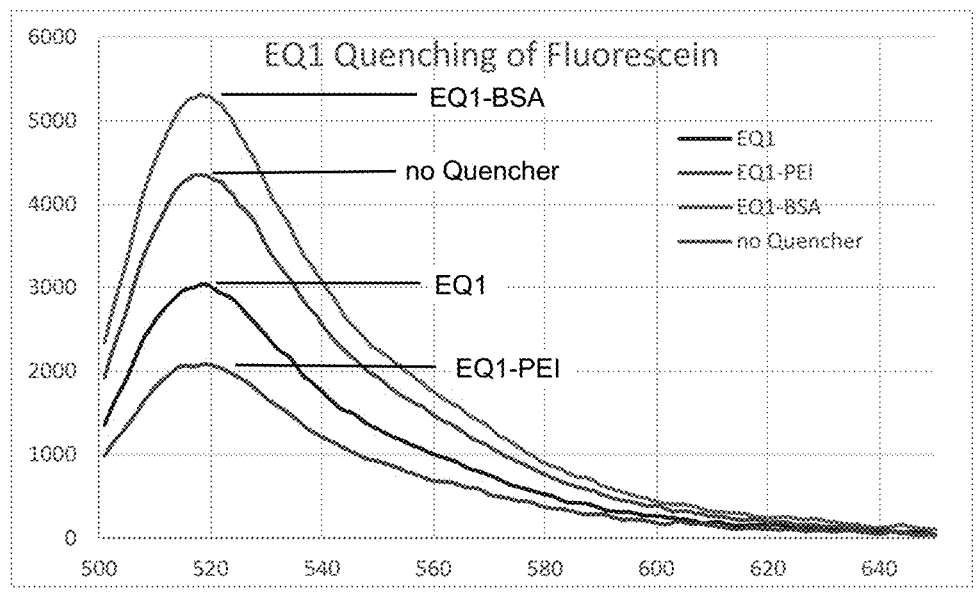
FIG. 3 shows the fluorescence quenching effect on phycoerythrin versus on a fluorescein-labeled antibody by a polymeric quencher embodiment of the invention and comparator compounds.

Next, to explore whether the enhancements of quenching with EQ1-PEI are specific to phycoerythrin, quenching of a fluorescein labeled antibody (FITC-anti Human IgG Fc, Biolegend 409309) was tested using EQ1 alone, EQ1-PEI, EQ1-BSA and no quencher control. Specifically, 400 ng of FITC labeled antibody was incubated with 394 pmoles of EQ1 alone, EQ1 attached to PEI (EQ1-PEI) or EQ1 attached to BSA (EQ1-BSA), or no quencher control. Again, the emission spectra was read with excitation at 480 nm. As shown in FIG. 3, although PEI-EQ1 does enhance quenching of fluorescein vs. EQ1 alone, it does not do so to nearly the same extent seen when quenching phycoerythrin.

Without limitation, the following embodiments are also provided by the invention.

Embodiment 1

A fluorescence quenching compound, including:
a plurality of discrete fluorescence quenching moieties; and
a polymer,
wherein each of the plurality of discrete fluorescence quenching moieties is chemically conjugated to a discrete site of the polymer.

Embodiment 2

The compound of embodiment 1, wherein the polymer is neither a polypeptide nor a polynucleic acid.

Embodiment 3

The compound of any one of the preceding embodiments, wherein the polymer is a branched polymer.

Embodiment 4

The compound of any one of the preceding embodiments, wherein the polymer is a polyamine polymer.

Embodiment 5

The compound of any one of the preceding embodiments wherein the polymer is a polycationic polymer.

Embodiment 6

The compound of any one of embodiments 1, wherein the polymer includes branched polyethylenimine.

Embodiment 7

The compound of embodiment 6, wherein the polymer is a branched polyethylenimine.

Embodiment 8

The compound of embodiment 6 or 7, wherein the branched polyethylenimine has a molecular weight of Mw 10,000 or greater.

Embodiment 9

The compound of embodiment 6 or 7, wherein the branched polyethylenimine has a molecular weight of Mw 10,000 or lower.

Embodiment 10

The compound of any one of the preceding embodiments, wherein the plurality of fluorescence quenching moieties include EQ1 as a moiety.

Embodiment 11

The compound of any one of embodiments 1-10, wherein the plurality of fluorescence quenching moieties include EQ2 as a moiety.

Embodiment 12

The compound of any one of embodiments 1-11, wherein the plurality of fluorescence quenching moieties include EQ0 as a moiety.

Embodiment 13

A composition including:
any one of the compounds of embodiments 1-12; and
a fluorescence emitter whose fluorescent emission is capable of being quenched by the compound.

Embodiment 14

The composition of embodiment 13, wherein the fluorescence emitter is a macromolecular fluorescence emitter.

Embodiment 15

The composition of embodiment 13 or 14, wherein the fluorescence emitter includes at least one polypeptide.

Embodiment 16

The composition of any one of embodiments 13-15, wherein the fluorescence emitter has a net negative charge.

Embodiment 17

The composition of embodiment 13, wherein the fluorescence emitter is a phycoerythrin.

Embodiment 18

The composition of any one of embodiments 13-17, wherein the fluorescent emission of the fluorescence emitter is quenched by the compound.

The invention also provides methods for quenching the fluorescent emission of a fluorescence emitter, such as any of the fluorescence emitters or types of fluorescence emitters disclosed herein, with or using any of the polymeric quenching compound embodiments disclosed herein. Similarly, invention also provides the use of any of the polymeric quenching compound embodiments disclosed herein to quench the fluorescent emission of a fluorescence emitter, such as any of the fluorescence emitters or types of fluorescence emitters disclosed herein.

It should be understood that wherever in the present application the term comprising or including (or a term of similar scope) is recited in connection with the description of any embodiment or part thereof, a corresponding embodiment or part thereof reciting instead the term consisting essentially of or the term consisting of (or a term of similar scope) is also disclosed.

Any and all publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s). Moreover, features described in connection with one embodiment of the invention may be used in conjunction with other embodiments, even if not explicitly exemplified in combination within.

What is claimed is:

1. A fluorescence quenching compound, comprising:
a plurality of discrete fluorescence quenching moieties; and a polyamine,
wherein each of the plurality of discrete fluorescence quenching moieties is chemically conjugated to a discrete site of the polyamine.

2. The compound of claim 1, wherein the polyamine is a branched polyamine.

3. The compound of claim 1, wherein the polyamine comprises branched polyethylenimine.

4. The compound of claim 3, wherein the polyamine is a branched polyethylenimine.

5. The compound of claim 3, wherein the branched polyethylenimine has a molecular weight of Mw 10,000 or greater.

6. The compound of claim 3, wherein the branched polyethylenimine has a molecular weight of Mw 10,000 or lower.

7. The compound of claim 1,
wherein the plurality of discrete fluorescence quenching moieties comprises

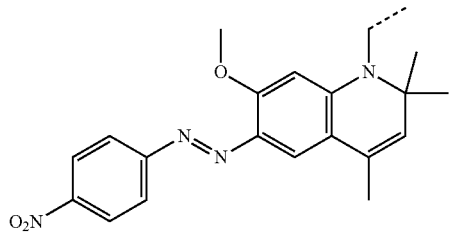

as a moiety.

8. The compound of claim 1,
wherein the plurality of fluorescence quenching moieties comprises

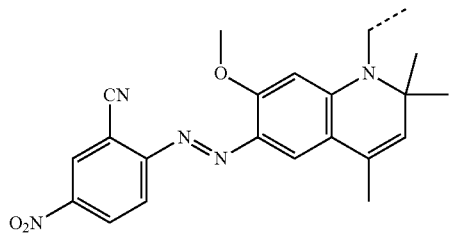

as a moiety.

9. The compound of claim 1,
wherein the plurality of fluorescence quenching moieties comprises

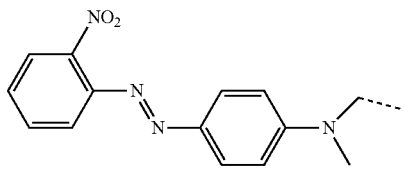

as a moiety.

10. The compound of claim 1,
   wherein the plurality of fluorescence quenching moieties comprises

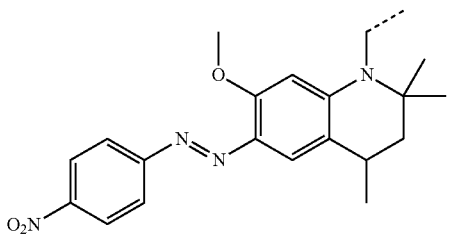

as a moiety.

11. The compound of claim 1,
   wherein the plurality of fluorescence quenching moieties comprises

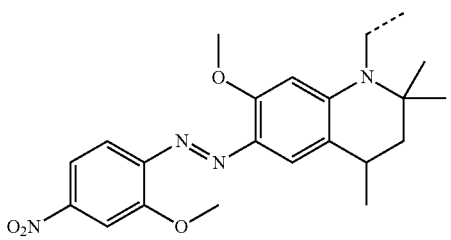

as a moiety.

12. The compound of claim 1,
   wherein the plurality of fluorescence quenching moieties comprises

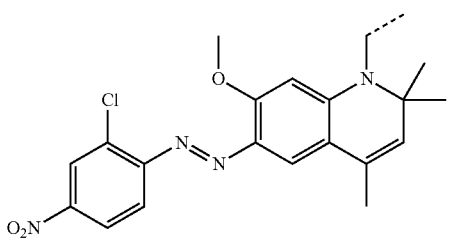

as a moiety.

13. The compound of claim 1,
   wherein the plurality of fluorescence quenching moieties comprises

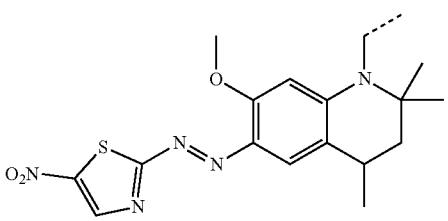

as a moiety.

14. The compound of claim 1,
   wherein the plurality of fluorescence quenching moieties comprises

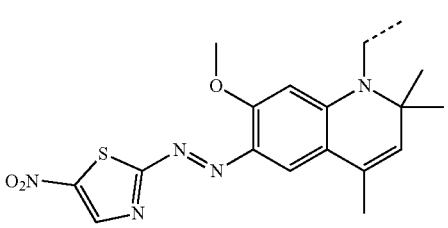

as a moiety.

15. The compound of claim 1,
   wherein the plurality of fluorescence quenching moieties comprises

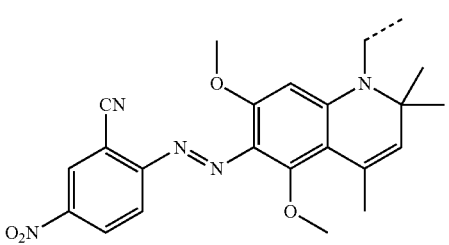

as a moiety.

* * * * *